United States Patent
Xiao et al.

(10) Patent No.: US 10,960,039 B2
(45) Date of Patent: Mar. 30, 2021

(54) COMPOSITION, PREPARATION METHOD AND USE OF THE SAME IN MANUFACTURE OF A PRODUCT FOR RELIEVING THYROID NODULES

(71) Applicant: INFINITUS (CHINA) COMPANY LTD., Guangdong (CN)

(72) Inventors: Lingyun Xiao, Guangdong (CN); Renhuai Cong, Guangdong (CN); Yuanyuan Wang, Guangdong (CN); Fangli Ma, Guangdong (CN); Chung Wah Ma, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 367 days.

(21) Appl. No.: 15/870,809

(22) Filed: Jan. 12, 2018

(65) Prior Publication Data
US 2018/0344793 A1    Dec. 6, 2018

(30) Foreign Application Priority Data
Jun. 6, 2017 (CN) .......................... 201710418127.9

(51) Int. Cl.
| | | |
|---|---|---|
| *A61K 36/284* | (2006.01) | |
| *A61K 36/236* | (2006.01) | |
| *A61P 5/14* | (2006.01) | |

(52) U.S. Cl.
CPC .......... *A61K 36/284* (2013.01); *A61K 36/236* (2013.01); *A61P 5/14* (2018.01); *A61K 2236/331* (2013.01); *A61K 2236/51* (2013.01)

(58) Field of Classification Search
CPC ................ A61K 36/236; A61K 36/284; A61K 2300/00; A61K 2236/331; A61K 2236/51; A61P 5/14
See application file for complete search history.

(56) References Cited

FOREIGN PATENT DOCUMENTS

| CN | 1280003 A | * | 1/2001 |
|---|---|---|---|
| CN | 1286992 A | * | 3/2001 |
| CN | 101721589 A | * | 6/2010 |
| CN | 102727717 A | * | 10/2012 |
| CN | 102755413 A | * | 10/2012 |
| CN | 105477359 A | * | 4/2016 |
| CN | 105535472 A | * | 5/2016 |
| CN | 105582300 A | * | 5/2016 |
| CN | 105641422 A | * | 6/2016 |
| CN | 105687710 A | * | 6/2016 |
| CN | 106138983 A | * | 11/2016 |
| CN | 109364123 A | * | 2/2019 |

OTHER PUBLICATIONS

First Office Action dated Oct. 23, 2020 for Chinese priority patent application No. 201710418127.9, English translation provided by Unitalen.
Feng Jianhua et al., TCM treatment of endocrine and metabolic diseases, People's Medical Publishing House, First Edition, Sep. 30, 2001, pp. 115-118.

* cited by examiner

*Primary Examiner* — Aaron J Kosar
(74) *Attorney, Agent, or Firm* — Yue (Robert) Xu; Apex Attorneys at Law, LLP

(57) ABSTRACT

The present disclosure relates to the technical field of health care products and foodstuffs, in particular to a composition, a preparation method, and the use thereof in preparation of products for relieving thyroid nodules. The composition provided by the invention uses *AtractylodisMacrocephalaeRhizoma* and *ChuanxiongRhizoma* as raw materials, which show synergistic effect through rational combination. Experiments show that the composition provided by the invention can improve thyroid epithelial cell proliferation and reduce the thyroid index of thyroid nodules, and has the advantages of relieving thyroid nodules and protecting thyroid function. The invention has the advantages of simple combination, high safety, simple and easy handling and definite cure effect.

1 Claim, 3 Drawing Sheets

3-1  3-2  3-3

COMPOSITION, PREPARATION METHOD AND USE OF THE SAME IN MANUFACTURE OF A PRODUCT FOR RELIEVING THYROID NODULES

CROSS REFERENCE TO RELATED APPLICATIONS

This application claims the priority of Chinese Patent Application No. 201710418127.9, filed on Jun. 6, 2017, and titled with "COMPOSITION, PREPARATION METHOD AND USE OF THE SAME IN MANUFACTURE OF A PRODUCT FOR RELIEVING THYROID NODULES", and the disclosures of which are hereby incorporated by reference.

FIELD

The present disclosure relates to the technical field of health care product and food stuff, specifically to a composition, preparation method, and use of the same in the manufacture of a product for relieving thyroid nodules.

BACKGROUND

Due to the stress from both work and daily life, the incidence of thyroid nodules is increasing in recent years, especially in middle-aged women, posing a threat to people's health. Epidemiological studies show that 5% women and 1% men have touchable thyroid nodules in iodine-sufficient regions. The detection rate of thyroid nodules by high-resolution ultrasound examination in randomly-selected people is 19%~67%. The incidence rate of thyroid cancer among thyroid nodules is 5%~10%.

Thyroid nodules can be classified into different types including hyperplastic nodular goiter, neoplastic nodule, cysts and inflammatory nodules. The occurrence of thyroid nodules is related to the genetic background and autoimmune environment of the individual, including many pathological changes such as thyroid degeneration, inflammatory response, autoimmune thyroid disease, traumatic and neoplastic changes. Regardless of the cause of thyroid nodules, the thyroid nodules always involve hyperplastic lesions of thyroid cells. Comprehensive therapies with a combination of surgery, radiotherapy and chemotherapy, as well as thyroid hormone suppression or supplement therapy, radioiodine therapy, laser coagulation therapy, high-frequency ultrasound ablation and the like, are usually adopted according to western medical practice. However, these treatments are effective only in a minority of people, accompanying with low cure rate, high side effects, adverse reactions and proneness to postoperative recurrence, due to the big individual difference and difficulty in handling. The efficacy and safety of some emerging technique (such as laser coagulation and high frequency focused ultrasound treatment) remain to be verified owing to lack of enough clinical data.

According to the Chinese traditional medicine theory, thyroid nodules belong to gallae, mostly caused by internal injury by emotional strains, improper diet and poor acclimatization, qi stagnation, phlegm coagulation and anterior cervical junction obstructing by blood stasis. "*Prescriptions for Succouring the Sick-Treatment of gallae*" recites: gallae are mostly caused by excess happiness, sorrow and worries. The qi and blood inside one's bodies circulate well when one maintains in peaceful mood. Otherwise, gallae are induced by qi stagnation and phlegm coagulation. Women are prone to thyroid nodules, which are mainly caused by phlegm coagulation, qi stagnation and blood stasis. The pathological characteristics could be summarized as deficiency for a manifestation of excess and mixed actual situation. The Chinese traditional medicine shows unique advantage for the treatment of thyroid nodules due to the merits including safety and convenience, easy handling, low cost, high cure rate and wide adaptability and the like.

There are some Chinese herbs for the treatment of thyroid diseases based on Chinese traditional medicine theory, however, most of them have complex ingredients and include many scarce and expensive crude drugs, which are not listed in the catalog of health care food and not safe. In view of the complexity of traditional ingredients, unclear targets and lack of pertinence in the treatment of thyroid nodules, it is necessary to develop a safe, effective product which targets the thyroid nodules.

SUMMARY

In view of the above, the technical problem to be solved by the present disclosure is to provide a composition, its preparation method and its application in the manufacture of products for relieving thyroid nodules. The composition provided by the present disclosure has simple ingredients and remarkable effect.

The present disclosure provides a composition, comprising 10~100 parts by mass of *Atractylodis Macrocephalae Rhizoma* and 10~100 parts by mass of *Chuanxiong Rhizoma*.

In the embodiments of the present disclosure, the composition comprises: 30~70 parts by mass of *Atractylodis Macrocephalae Rhizoma* and 30~70 parts by mass of *Chuanxiong Rhizoma*.

In some embodiments, the composition comprises: 30 parts by mass of *Atractylodis Macrocephalae Rhizoma* and 70 parts by mass of *Chuanxiong Rhizoma*.

In some embodiments, the composition comprises: 70 parts by mass of *Atractylodis Macrocephalae Rhizoma* and 30 parts by mass of *Chuanxiong Rhizoma*.

In some embodiments, the composition comprises: 10 parts by mass of *Atractylodis Macrocephalae Rhizoma* and 100 parts by mass of *Chuanxiong Rhizoma*.

In some embodiments, the composition comprises: 100 parts by mass of *Atractylodis Macrocephalae Rhizoma* and 10 parts by mass of *Chuanxiong Rhizoma*.

In some embodiments, the composition comprises: 50 parts by mass of *Atractylodis Macrocephalae Rhizoma* and 50 parts by mass of *Chuanxiong Rhizoma*.

*Atractylodis Macrocephalae Rhizoma* is the dried rootstock of *Atractylodes macrocephala* Koidz. from *Atractylodes, Asteraceae*. It is warm in nature and has a taste of sweet and bitter, which has a function on spleen and stomach meridians. It has an efficacy of clearing damp and promoting diuresis, arresting sweating and preventing miscarriage, strengthening spleen and benefiting qi. It is usually used for the treatment of diseases including deficiency of spleen and less diet, abdominal distension and diarrhea, phlegm and retained fluid, dizziness and palpitation, edema, spontaneous sweating, Fetal irritability and the like. *Atractylodis Macrocephalae Rhizoma* has the effect of anti-bacteria, anti-aging, anti-tumor and the like, with impacts on nervous system, uterine smooth muscle and gastrointestinal motility and the ability to effectively regulate immune function. *Chuanxiong Rhizoma* is the dried rootstock of *Ligusticum chuanxiong* Hort. from Umbelliferae, first recorded in "Sheng Nong's herbal classic". It is warm in nature, tastes pungent and a little bitter, with the efficacy of promoting blood circulation and activating qi-flowing. It could be used for the treatment of thoracic obstruction and cardiodynia, pricking pain in the chest, flutter swelling pain, irregular menstruation, amenorrhea and dysmenorrheal, gynecologic abdominal lumps-caused abdominal pain, headache, rheumatic arthralgia and the like. The present disclosure further provides an extract, prepared from the composition disclosed by the present disclosure.

A method of preparing the extract of the present disclosure, comprising: extracting the composition of the present disclosure with water and concentrating the composition to obtain the extract.

The temperature for water extraction is 100° C. and the duration time is 1.5 h~2.5 h.

In some embodiments, the temperature is 100° C. and the duration time is 2 h.

In some embodiments, the water mass for the extraction is 8 to 12 times of the composition mass.

In some particular embodiments, the water mass is 10 times of the composition mass.

In some embodiments, water extraction is carried out twice.

In particular, the extraction process comprises:

adding 10 times of water to the composition provided by the present disclosure, extracting at 100° C. for 2 h and isolating the extract solution; adding 10 times of water to the precipitate again, extracting at 100° C. for 2 h and isolating the extract solution; combining the extract solution from the above two extraction steps and concentrating to obtain the extract.

The extract in the present disclosure is prepared under atmospheric pressure.

In some embodiments, the extraction solution is concentrated by 8~12 times.

In some particular embodiments, the extraction solution is concentrated by 10 times.

The present disclosure provides the use of the composition or extract in the manufacture of product for relieving thyroid nodules.

The present disclosure further provides a product for relieving thyroid nodules, comprising the extract provided by the present disclosure.

The product for relieving thyroid nodules provided by the present disclosure can be manufactured into solid or liquid preparations;

The dosage form of the solid preparation is selected from the group comprising tablets, capsules, granules, pills, dropping pills, mixture and powder;

the dosage form of the liquid preparation is selected from the group comprising oral liquid, soft capsule or aerosol.

The materials for the composition provided by the present disclosure are *Macrocephalae Rhizoma* and *Chuanxiong Rhizoma*, which show synergistic effect by rational combination. The composition provided by the present disclosure can improve the thyroid epithelial cell proliferation and reduce the thyroid index of thyroid nodules, thus relieving thyroid nodules and protecting the thyroid gland. Meanwhile, the present disclosure has the advantages of simple combination, high safety, simple and convenient handling and definite cure effect.

BRIEF DESCRIPTION OF DRAWINGS

FIG. 3 shows morphological changes of thyroid follicles after administration of the composition; wherein, FIG. 3-1 shows the volume of thyroid follicles in blank group; FIG. 3-2 shows the volume of thyroid follicles in model group; FIG. 3-3 shows the volume of thyroid follicles after administration of the composition prepared in Example 1.

DETAILED DESCRIPTION

Figure 1:
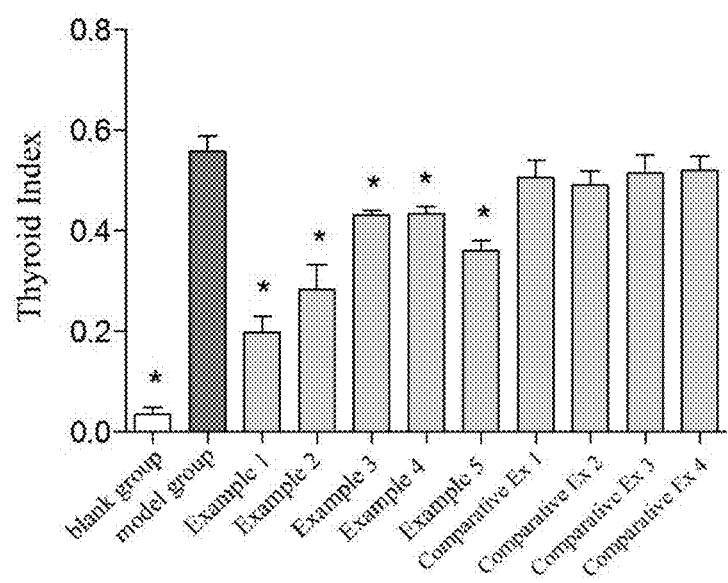
FIG. 1 shows the thyroid index in each group of animals; *p<0.05, indicates significant difference with model group.

The present disclosure provides a composition and its preparation method and its use in manufacture of products for relieving thyroid nodules. Those skilled in the art can learn from the contents herein and improve the process parameters as appropriate. It is specifically to be noted that all similar substitutions and modifications will be apparent to those skilled in the art and are to be considered as included in the present disclosure. The method and application of the present disclosure have been described with reference to the preferred embodiments. Apparently, those skilled in the art can make modifications and changes to the methods and applications herein without departing from the content, spirit and scope of the present disclosure, to realize and use the present disclosure.

The reagents and equipment used in the present disclosure are all commercially available in the market.

The present disclosure is further illustrated with reference to the examples below.

EXAMPLE 1

1000 g water was added to 50 g *Macrocephalae Rhizoma* and 50 g *Chuanxiong Rhizoma*; the mixture was boiled and kept boiling (100° C.) for 2 h. Extraction solution was isolated and the filtration residue was collected. 1000 g water was added again to the residue, which was then boiled and kept boiling (100° C.) for 2 h. The two filtrates were combined and concentrated to 100 mL to obtain the extract.

EXAMPLE 2

1000 g water was added to 30 g *Macrocephalae Rhizoma* and 70 g *Chuanxiong Rhizoma*; the mixture was boiled and kept boiling (100° C.) for 2 h. Extraction solution was isolated and the filtration residue was collected. 1000 g water was added again to the residue, which was then boiled and kept boiling (100° C.) for 2 h. The two filtrates were combined and concentrated to 100 mL to obtain the extract.

EXAMPLE 3

1000 g water was added to 70 g *Macrocephalae Rhizoma* and 30 g *Chuanxiong Rhizoma*; the mixture was boiled and kept boiling (100° C.) for 2 h. Extraction solution was isolated and the filtration residue was collected. 1000 g water was added again to the residue, which was then boiled and kept boiling (100° C.) for 2 h. The two filtrates were combined and concentrated to 100 mL to obtain the extract.

EXAMPLE 4

1100 g water was added to 10 g *Macrocephalae Rhizoma* and 100 g *Chuanxiong Rhizoma*; the mixture was boiled and kept boiling (100° C.) for 2 h. Extraction solution was isolated and the filtration residue was collected. 1100 g water was added again to the residue, which was then boiled and kept boiling (100° C.) for 2 h. The two filtrates were combined and concentrated to 110 mL to obtain the extract.

EXAMPLE 5

1100 g water was added to 100 g *Macrocephalae Rhizoma* and 10 g *Chuanxiong Rhizoma*; the mixture was boiled and kept boiling (100° C.) for 2 h. Extraction solution was isolated and the filtration residue was collected. 1100 g water was added again to the residue, which was then boiled and kept boiling (100° C.) for 2 h. The two filtrates were combined and concentrated to 110 mL to obtain the extract.

Comparative Example 1

1100 g water was added to 5 g *Macrocephalae Rhizoma* and 110 g *Chuanxiong Rhizoma*; the mixture was boiled and kept boiling (100° C.) for 2 h. Extraction solution was isolated and the filtration residue was collected. 1100 g water was added again to the residue, which was then boiled and kept boiling (100° C.) for 2 h. The two filtrates were combined and concentrated to 110 mL to obtain the extract.

Comparative Example 2

1100 g water was added to 105 g *Macrocephalae Rhizoma* and 5 g *Chuanxiong Rhizoma*; the mixture was then boiled and kept boiling (100° C.) for 2 h. Extraction solution was isolated and the filtration residue was collected. 1100 g water was added again to the residue, which was then boiled and kept boiling (100° C.) for 2 h. The two filtrates were combined and concentrated to 110 mL to obtain the extract.

Comparative Example 3

1000 g water was added to 100 g *Macrocephalae Rhizoma*; the mixture was boiled and kept boiling (100° C.) for 2 h. Extraction solution was isolated and the filtration residue was collected. 1000 g water was added again to the residue, which was then boiled and kept boiling (100° C.) for 2 h. The two filtrates were combined and concentrated to 100 mL to obtain the extract.

Comparative Example 4

1000 g water was added to 100 g *Chuanxiong Rhizoma*; the mixture was boiled and kept boiling (100° C.) for 2 h. Extraction solution was isolated and the filtration residue was collected. 1000 g water was added again to the residue, which was then boiled and kept boiling (100° C.) for 2 h. The two filtrates were combined and concentrated to 100 mL to obtain the extract.

Pharmacodynamics Study

In order to verify the efficacy of the Chinese traditional medicine composition, extracts from Examples 1-5 and Comparative Examples 1-6 are subjected to efficacy test as follows:

1. Purpose

Study the efficacy of a Chinese traditional medicine composition.

2. Materials 2.1 Samples

The extracts from Examples 1-5 and Comparative Examples 1-6

2.2 Experimental Animals

Healthy SD female rat, weigh 160~180 g, SPF class.

3 Experimental Procedures 3.1 Model establishment and drug administration

The rats were randomly divided into three groups: blank control group, model group, model group with extract from Example 1, Example 2, Example 3, Example 4, Example 5, Comparative Example 1, Comparative Example 2, Comparative Example 3, Comparative Example 4, Comparative Example 5 and Comparative Example 6, respectively. The blank control group was administered with the same amount of normal saline while other groups were administered intragastrically with 0.2% propylthiouracil (PTU) (0.5 ml/100 g body weight) once a day, for three consecutive weeks. After three weeks, the animals in each group were administrated with the corresponding drugs by gavage once a day for five consecutive weeks, meanwhile, PTU was added into drinking water to reach the maintenance dose. The model group was given PTU maintenance dose; the blank control group was given equal amount of distilled water.

3.2 Thyroid Weight

The animals were sacrificed at the end of the administration. Thyroid tissues of which were isolated and weighed, and the thyroid index (thyroid/body weight ($\times 10^3 \times 100\%$)) of each group was compared.

3.3 Proliferation of Thyroid Cells

The expression of Ki-67 was detected by immunochemistry. Ten visual fields under high magnification were selected randomly, and the number of Ki-67 positive cells in 200 thyroid cells was counted in each field to compare the proliferation of thyroid cells (K-67 positive thyroid cells/total thyroid cells$\times 100\%$).

3.4 Pathological Examination

The rats were sacrificed at the end of the administration. The thyroid tissues of which were isolated, fixed with 4% paraformaldehyde and subjected to paraffin embedding and sectioning for HE staining.

4. Results 4.1 Thyroid Index (see FIG. 1)

The thyroid index in model group was significantly higher than the blank control group when comparing the thyroid index. The extracts (Examples 1-5 and Comparative examples 1-4) reduced the thyroid index to some extent in each group; extracts of Comparative Examples 1 to 4 have a significantly ($p<0.05$) lower efficacy than those of Examples 1 to 5. The rats administered with extracts of Examples 1 to 5 has significantly lower thyroid index, indicating that the extracts of Examples 1 to 5 remarkably relieved the formation of thyroid nodules, wherein the extract of Example 1 has the most prominent protective effect which is significantly ($p<0.05$) better than those of Examples 2 to 5.

4.2 Proliferation of Thyroid Cells

The proliferation in model group was significantly higher than the blank control group when comparing proliferation of thyroid cells. The extracts (Examples 1-5 and Comparative examples 1-4) could reduce the proliferation to some extent in each group; however, extracts of Comparative examples 1 to 4 have minor protective effect which is significantly ($p<0.05$) less than those of Examples 1 to 5. The extract of Example 1 has the most prominent effect of inhibiting the proliferation of thyroid cells among those of Examples 1 to 5, which is significantly ($p<0.05$) higher than those of Examples 2 to 5.

4.3 Pathological Examination

Figure 2:
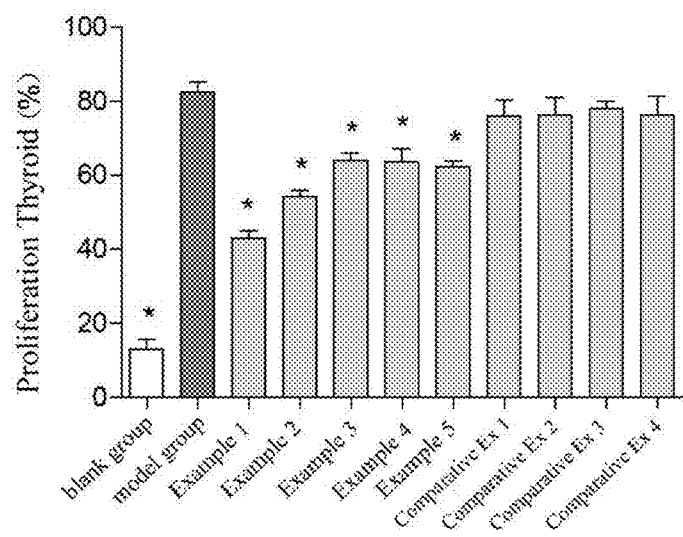
FIG. 2 shows the proliferation of thyroid cells in each group of animals; *p<0.05, indicates significant difference with model group.
Figure 3:
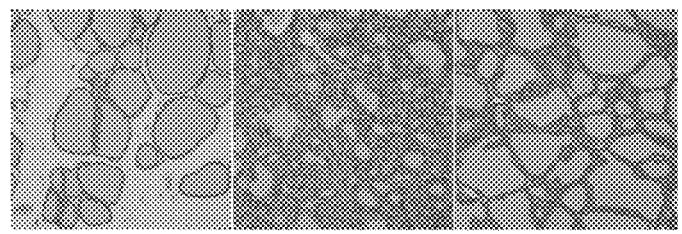

As shown in FIG. 3, under optic microscope (HE$\times 200$), FIG. 3-1 shows that the thyroid follicles have a medium size and a round or oval shape, with full follicular cavities, rich in colloid. The follicular epithelial cells are in regular cubic shape and arranged into a single layer, without interstitial hyperplasia. FIG. 3-2 shows that the model group has more follicles while smaller cavities, and the colloid inside the cavities is reduced significantly or absent. The follicular epithelial cells have both hyperplasia and hypertrophy with irregular multi-layer arrangement. FIG. 3-3 shows that the hyperplasia of thyroid follicles in in rats administered with the extracts of Example 1 is alleviated significantly. The proliferation of cells in rats administered with the extracts of other Examples (Examples 2 to 5) was similar to that of Example 1, but none of the results is better than Example 1. The extracts of Comparative examples 1 to 4 have poor effect.

The above are only the preferred embodiments of the present disclosure, and it should be noted that those skilled in the art may make some improvements and modifications without departing from the principle of the present disclosure, and these improvements and modifications should also be deemed within the scope of the present disclosure.

What is claimed is:

1. A method for relieving thyroid nodules comprising administrating an effective amount of a composition to a human subject in need thereof;
    wherein the composition is made from 10 to 100 parts by mass of *Atractylodis Macrocephalae Rhizoma* and 10 to 100 parts by mass of *Chuanxiong Rhizoma*, wherein *Atractylodis Macrocephalae Rhizoma* and *Chuanxiong Rhizoma* are used as the only active materials.

* * * * *